United States Patent [19]
Steinel

[11] Patent Number: 5,940,577
[45] Date of Patent: Aug. 17, 1999

[54] ELECTRIC DEVICE FOR THE VAPORIZATION OF ADDITIVES

[75] Inventor: Heinrich Wolfgang Steinel, Bad Wörishofen, Germany

[73] Assignee: Steinel GmbH & Co. KG, Herzebrock-Clarholz, Germany

[21] Appl. No.: 08/776,292

[22] PCT Filed: Jul. 25, 1995

[86] PCT No.: PCT/EP95/02942

§ 371 Date: Jun. 9, 1997

§ 102(e) Date: Jun. 9, 1997

[87] PCT Pub. No.: WO96/04022

PCT Pub. Date: Feb. 15, 1996

[30] Foreign Application Priority Data

Aug. 3, 1994 [EP] European Pat. Off. ............. 94112154

[51] Int. Cl.$^6$ .............................. A61M 16/00; F24F 6/08
[52] U.S. Cl. ......................................... 392/395; 392/392
[58] Field of Search ................................... 392/392, 394, 392/395; 338/22 R, 23; 219/542, 544

[56] References Cited

U.S. PATENT DOCUMENTS

| | | | |
|---|---|---|---|
| 1,994,932 | 3/1935 | Vidal | 392/395 |
| 3,996,447 | 12/1976 | Bouffard et al. | 338/22 R |
| 4,544,829 | 10/1985 | Adachi et al. | 338/22 R |
| 4,874,924 | 10/1989 | Yamanoto et al. | 392/395 |
| 5,038,394 | 8/1991 | Hasegawa et al. | 392/395 |
| 5,095,647 | 3/1992 | Zobele et al. | 392/395 |
| 5,222,186 | 6/1993 | Schimanski et al. | 392/395 |
| 5,484,086 | 1/1996 | Pu | 392/395 |

FOREIGN PATENT DOCUMENTS

| | | |
|---|---|---|
| A 0 290 159 | 11/1988 | European Pat. Off. |
| 90 14 309 U | 12/1990 | Germany . |
| 91 04 709 U | 6/1991 | Germany . |
| WO 88 05310 | 7/1988 | WIPO . |

*Primary Examiner*—Teresa Walberg
*Assistant Examiner*—Sam Paik
*Attorney, Agent, or Firm*—Darby & Darby

[57] ABSTRACT

An electric device for vaporization of additives having a housing with an electric heating disposed therein. The heating includes a heating element and a heat exchanger, to supply the heat generated by the heating element to the heat exchanger and to convey it to the substance to be vaporized. The heating element is a PTC element, clamped between two electrodes and at least one of the two electrodes is disposed in proximity to the heat exchanger and is integrally formed with it.

9 Claims, 4 Drawing Sheets

ELECTRIC DEVICE FOR THE VAPORIZATION OF ADDITIVES

FIELD OF THE INVENTION

The present invention refers to an electric device for the vaporization of additives.

BACKGROUND OF THE INVENTION

A generic device of that kind comprises a housing with an electric heating disposed therein, having a heating element and a heat exchanger, to supply the heat generated by the heating element to the heat exchanger and to convey the heat to the substance to be vaporized.

The object of the invention is to further develop a device of that kind so that it can be easily manufactured and works at low electrical power loss.

This object is achieved by a device comprising the features of The solution according to the invention is characterized in that the heating element is a PTC element, clamped between two electrodes, and that at least one of the two electrodes is disposed in proximity to the heat exchanger and is integrally formed therewith.

By providing the heating, it is achieved that the electrodes for the electric heating element at the same time serve the purpose of supplying the heat released by the heating element to the heat exchanger. Since the electrodes are integrally formed with the heat exchanger, the device consists of only few parts, so that the device can be easily manufactured at low cost. Furthermore, the device according to the invention has a good heat conductivity between the heating element and the heat exchanger so that the power loss can be kept low.

In one embodiment, the device comprises a container connectable to the housing for the substance to be evaporated, in which a wick is disposed, and the heat exchanger comprises a passage channel which surrounds the wick.

The heat exchanger is preferrably provided annularly, having a molded section, extending coaxially to the wick. In this embodiment of the heat exchanger, a good coupling of the heat to the wick takes place, which results in a good efficiency of the device.

In an alternative embodiment, the heat exchanger is provided as a planar heating surface, which serves as a supporting surface for a container for the substance to be evaporated. In this embodiment, a direct influence of the heat released by the heat exchanger on the entire substance to be evaporated is enabled by the direct proximity of the container to the heating surface.

The electrodes and/or the heat exchanger are preferrably provided with connecting conduits integrally formed therewith. By integrally forming the electrodes, the heat exchanger and the connecting conduits, the number of parts is reduced, which simplifies the manufacture of the device, since the conventional strand connections can be avoided and almost all electric parts can be manufactured on a common punch member.

It is of advantage if the connecting conduits, the heat exchanger and the electrodes are integrally formed on a punching sheet, which is bent if necessary after punching, and which is coated by a plastic material at the points at which an increased inherent stability or heat insulation is required. This considerably simplifies the manufacture of the device, since all parts can be manufactured from a planar workpiece by use of production machines.

In a further preferred embodiment, a region having a reduced wire cross section is provided between the connecting conduits and the electrodes or the heat exchanger, said region providing a sufficient electrical contact for the electrodes, but hardly conducts the heat. Thereby a loss of heat through the connecting conduits is avoided to a great extent.

In a further embodiment of the invention, the electrodes are surrounded by the plastic material on the sides opposite one another, and comprise a web on the sides facing one another at the outer edge of the electrodes. The PTC element disposed between the electrodes is thereby held in form-fit fashion between the webs, so that additional holding elements for the heating element are not necessary.

Preferrably, a resilient element is disposed between an electrode and the PTC element, and a clamping element clamps the two electrodes and the PTC element disposed between the two electrodes. In this arrangement, a close contact of the electrodes to the PTC element is achieved, which not only leads to a tight electrical connection, but also improves the heat coupling between the heating element and the electrodes.

BRIEF DESCRIPTION OF THE DRAWINGS

The present invention will new be explained by the aid of embodiments under reference to the drawings.

DETAILED DESCRIPTION OF THE INVENTION

Figure 1:
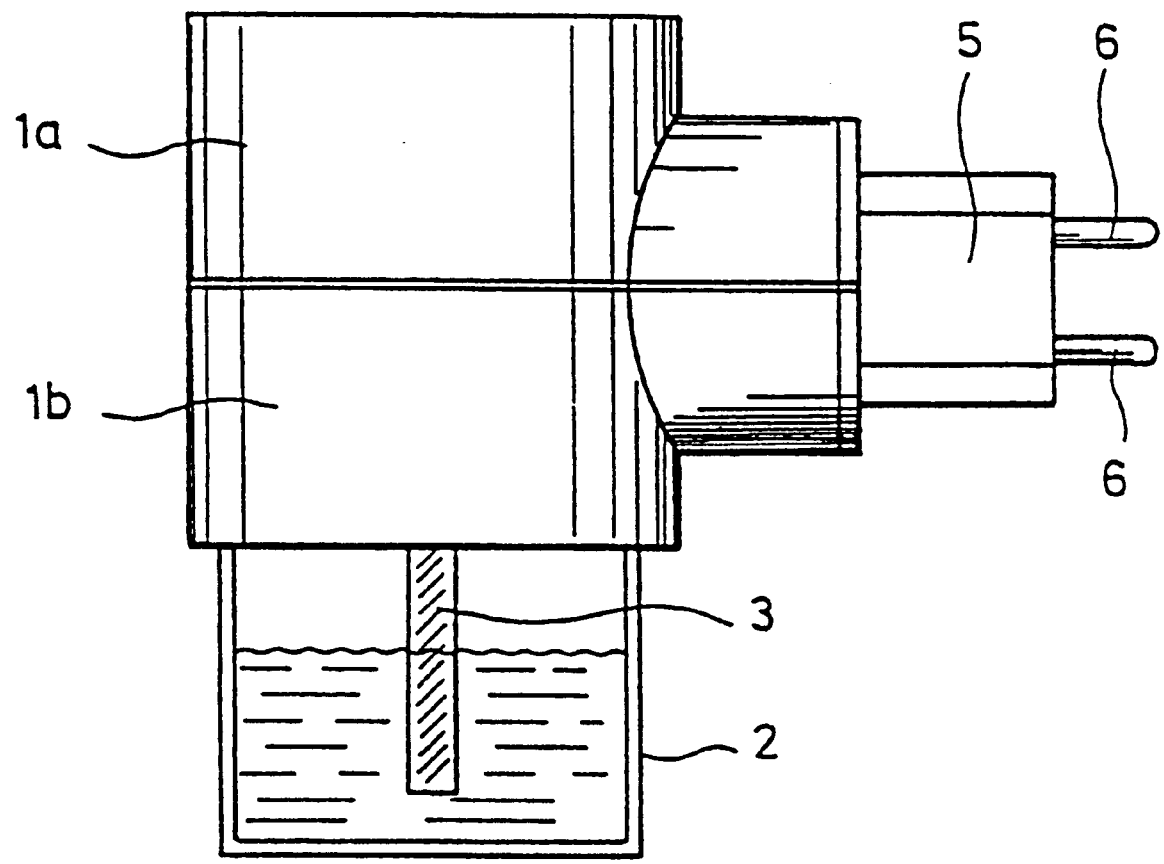
FIG. 1 is a lateral view of the device.

According to FIG. 1, the device comprises a housing consisting of two semimonocoque parts of the housing 1a, 1b, with a container 2 connectable thereto, in which the substance to be vaporized is located, e.g. a liquid with additives resolved therein. The attachment means between the housing and the container 2 consist of an external thread attached at the upper end of the container and a respective internal thread formed in the lower semimonocoque part of the housing 1b. A wick 3 is disposed within the container 2, consisting of carbon fibers or textile threads. The liquid to be vaporized is transported through the wick to the heating 4, closer defined in FIGS. 2 and 3. A plug 5 with two plug contacts 6 attached thereto is rotatably supported within the housing. As can be derived from FIG. 4, the plug comprises an annular groove 7, which engages a correspondingly formed edge of the semimonocoque parts of the housings 1a, 1b, if the housing is closed.

Figure 2:
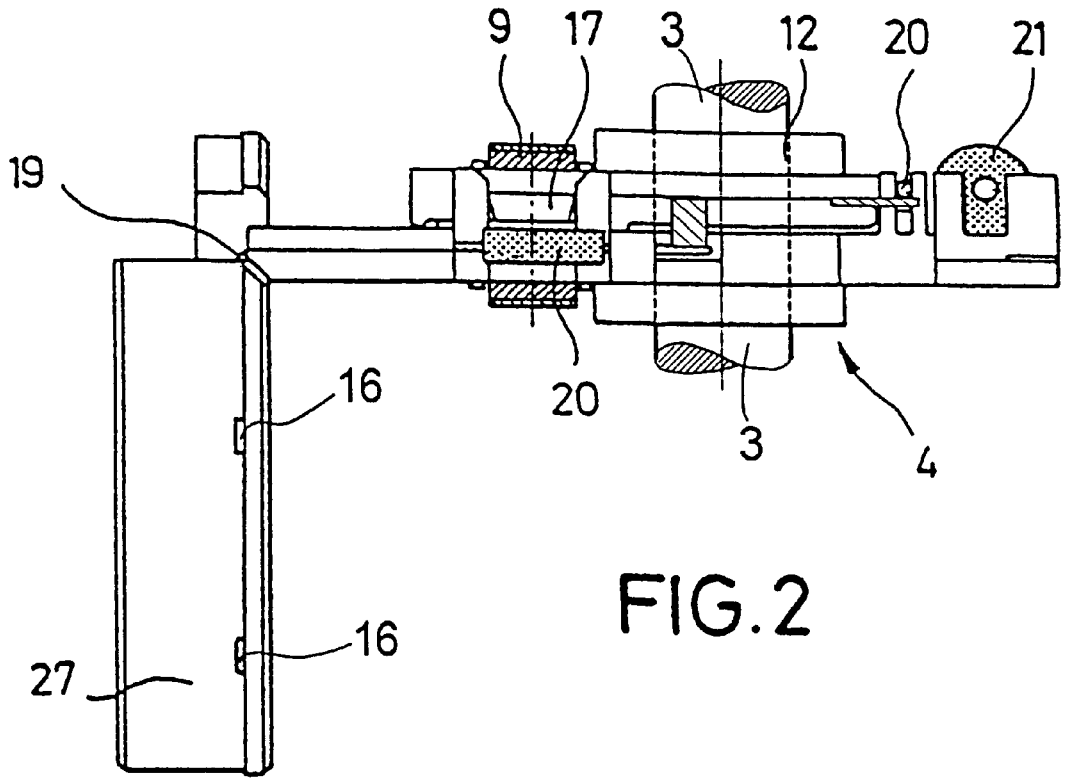
FIG. 2 is a lateral view of the heating of the device disposed within the housing.
Figure 3:
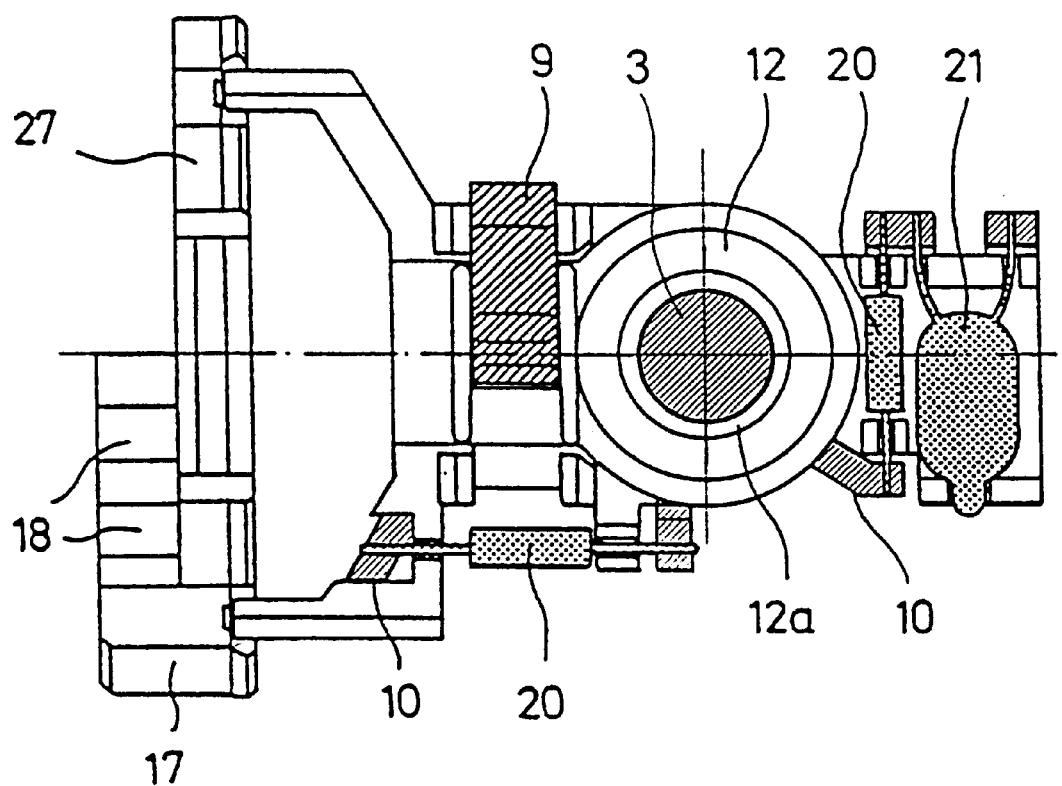
FIG. 3 is a top view of the heating, shown in FIG. 2.

The heating 4 comprises a PTC heating element clamped between two electrodes 8 disposed on top of each other, not directly shown in FIG. 2 and 3, since the most part of the electrodes is coated by a heat resistant and insulating plastic material and prevents a free sight to the PTC element. The electrodes are embedded in the plastic material on the opposite side. The sides facing each other comprise a contact surface, which is large enough to completely contact the PTC element. A continuous web is formed along the outer edge of the electrodes, wherein the webs are disposed on the upper and lower electrode in a manner that they mesh with one another. Thereby, a closed cavity is formed, with which the PTC element is retained in form-fit fashion. A resilient, conductive element is disposed between the lower electrode an the PTC element, which, together with a U-shaped clamping spring 9 surrounding the electrodes from the outside, is responsible for a good contact between the electrodes and the PTC element. The electric part of the heating furthermore comprises connecting conduits 10, a part of which being connected through a region 11 having a reduced wire cross section to the electrodes 8, as can be seen more clearly in FIG. 6.

Figure 7:
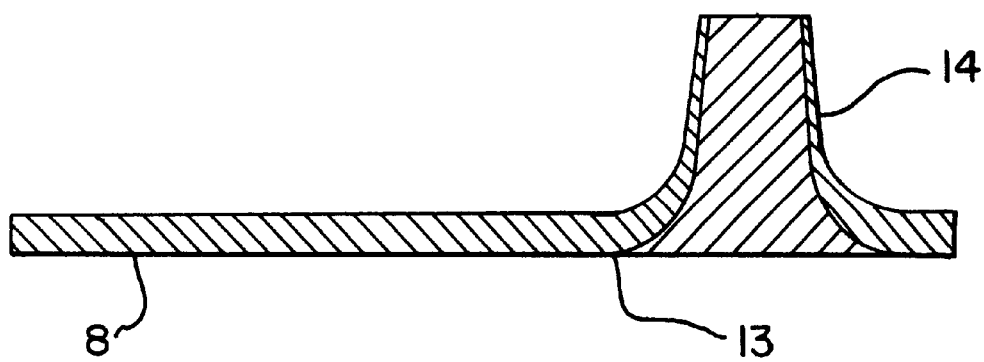
FIG. 7 is a magnified section of an electrode with a heat exchanger formed integrally therewith.

A heat exchanger 12 consists of two annular sections 13 disposed on top of one another, which comprise a molded section 14 made of the same metallic material as the electrodes. As can be seen in FIG. 7, the ratio between the length of the molded region 13 to the thickness of the electrode is approximately 6:1. The molding process is performed in a manner that the material strength of the molded region diminishes towards the free end thereof. It is in particular important in molding that sufficient material is existing at the point between the molded section 14 and the annular section 13 so that a good heat transition is ensured on the molded part. The greater material thickness at the points, which are close to the heating element, leads to the result that the heating energy is transmitted well up to the outer ends. The annular and molded region 13 or 14 is completely embedded in the plastic material. The coated, annular and molded regions of the heat exchanger can be seen in FIG. 3, said heat exchanger comprising an axially centered passage channel 12a. The annular region is coated with a thin insulation material at the inner wall thereof, so that as much heat energy as possible can be conducted into the passage channel 12a. The outer wall of the annular region in turn, has a thick insulating layer, which becomes thicker towards the free end in the axial direction of the molded region. An insulation formed in that manner reduces the heat losses and is responsible that the heat transmitted in this manner is transported exactly to the desired point in the passage channel.

The essential steps of manufacturing a device according to the present invention will now be explained.

Figure 6:
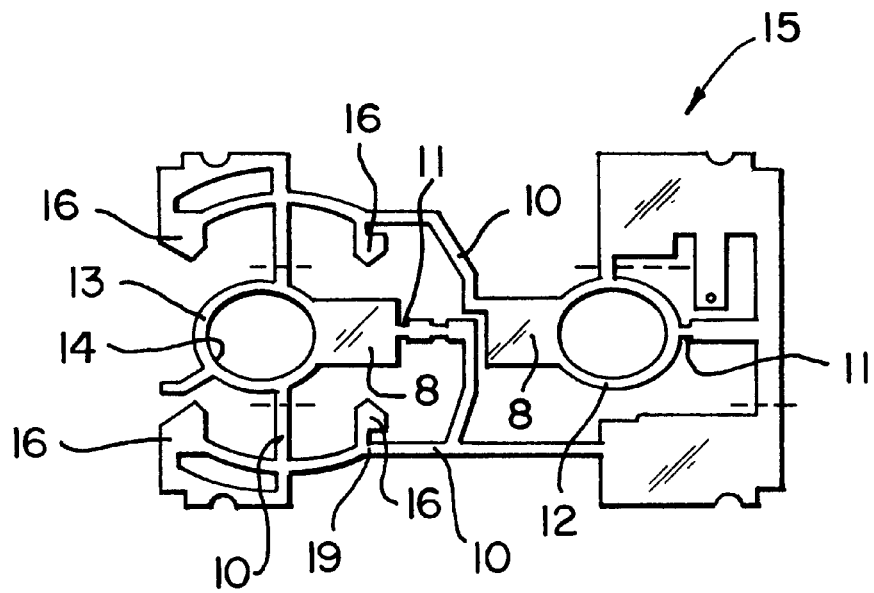
FIG. 6 is a view of the punching sheet member, containing essential parts of the device.

FIG. 6 shows a punching sheet part 15 with the essential parts of the electric heating. In the completely punched condition, the sheet portions, shown in dotted lines in the drawing, are completely separated. Two electrodes 8 can be seen, with annular portions 13, formed integrally with the electrodes, each comprising a molded section 14. Connecting conduits 10 are integrally formed with the electrodes 8 and the annular section 13, partially via regions 11 having a reduced cross section. The connecting conduits are provided in the left half of the punching member, shown in FIG. 6, having the shape of a quarter of a ring and facing each other, and each of them carry a pair of contacts offset about 90°.

In a further method step, the punching sheet member is coated by a plastic material at the points at which an increased inherent stability or heat insulation is required. The coating of the rings having the shape of a quarter of a ring is carried out so that an almost closed ring is formed, with the contacts 16 projecting radially inwardly at the inner wall thereof. A web 17 is formed at the front side of the ring, said web extending in the axial direction of the ring. The web extends at a length of approximately a fourth of the ring and comprises a plurality of recesses 18 with bevelled surfaces (FIG. 3) at its inner wall. After the coating process, the spots shown with dotted lines in FIG. 6 are separated, which causes the electrode, shown in the left half, to completely fall out. Then, the connecting conduits, having the shape of a quarter of a ring, embedded into the almost closed ring, are bent at the portions 19 about 90° with respect to the remaining electric part of the heating, which can be seen in FIG. 2.

Finally, the heating is totally provided with resistors 20 and a light emitting diode 21.

During operation of the device, the electric circuit of the heating functions as follows: Starting at a connecting conduit 10, the heating current flows through safety resistor 20 to the upper annular section 13, integrally formed with the upper electrode 8. From this electrode, the current flows through the PTC heating element to the lower electrode 8 and then to a second connecting conduit 10, which is completely coated by a plastic material. The two connecting conduits 10 are connected with the plug contacts 6 of the plug 5, shown in FIG. 1. A protective resistor 20 is connected in parallel to the pair of electrodes 8, with a light emitting diode 21 connected in series thereto. The connecting conduits for the protective resistor and the light emitting diode are located at the upper and the lower annular section 13 of the heat exchanger 12.

PTC heating elements are known to stabilize themselves at a temperature depending on their dimensions. For the present embodiment, the PTC heating element was chosen so that it generates a temperature of 150° C. at the predefined operating voltage. Since the upper and the lower electrode 8 are in tight contact with the heating element, and the annular sections are integrally formed with the molded portion at the heating element, the heat generated by the heating element is transported to the heat exchanger 12. Based on the embodiment of the device according to the invention, the heat loss is so low that a temperature of approximately 128° C. is measured in the passage channel at the wick. The small temperature loss of only 22° C. with respect to the operating temperature of the PTC is remarkable. Furthermore a very small fluctuation of temperature of only 0.5° C. has been proven during long-time tests.

It has to be pointed to the fact, that the heating, which was described in the embodiment, is only an example and that a lot more of technical possibilities exist for realizing this heating. The heating element, for example, does not necessarily have to consist of a PTC heating element, but can also be a heating winding made of a heating wire, which is embedded in a ceramic heating body.

A different embodiment of the present invention, not shown in the drawings, differs from the above-mentioned embodiment by a different heat exchanger 8. In this embodiment, the annular section 13 and the molded section 14 are replaced by a planar heating surface. Furthermore, a container is provided which is located above the heating surface, e.g. a heat resistant plastic bowl, instead of the container 2 with the wick retained therein. The substance to be evaporated is situated in the bowl, which is regularly heated by the heating surface disposed directly underneath the bowl. In this embodiment the housing comprises a suitable opening, through which the container can be supplied with the substance to be evaporated.

Figure 4:
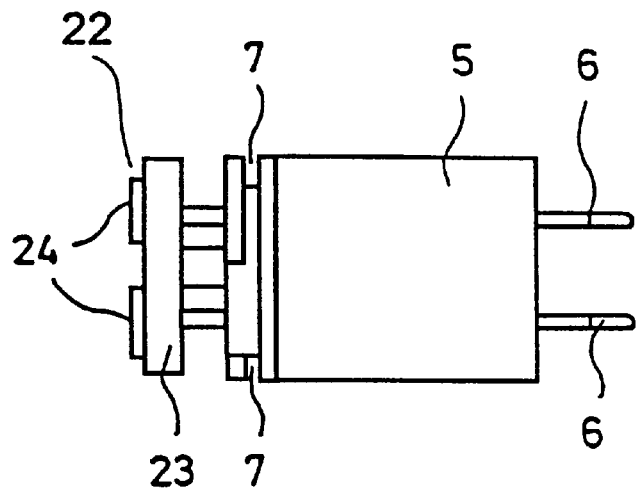
FIG. 4 is a lateral view to the plug and the first rotating joint member of the present invention.
Figure 5:
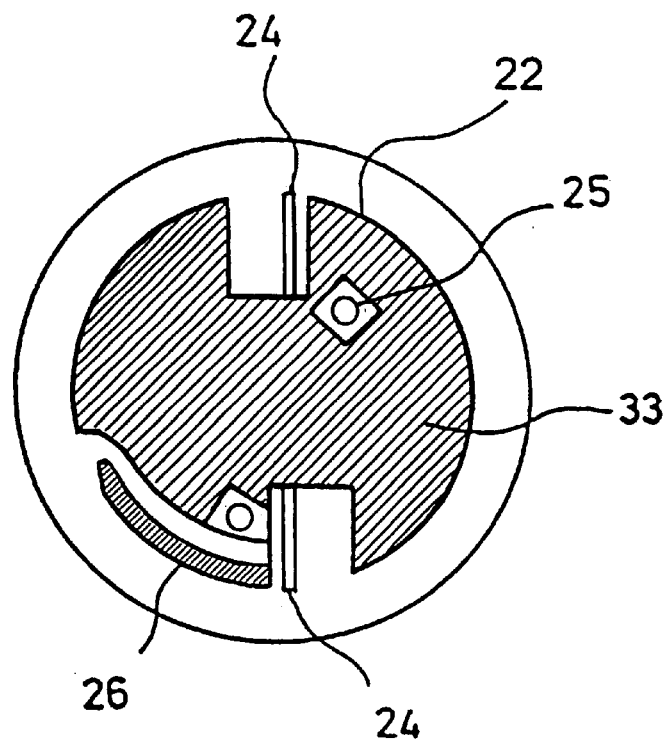
FIG. 5 is s front view of the first rotating joint member.

It will new be referred to FIG. 4 and 5, which describe a first rotating joint member 22:

The first rotating joint member 22 is rigidly connected to the plug 5 and basically consists of a disk-like carrier portion 23, carrying two opposing strip-like electric contacts 24. The electric contacts 24 are connected to the plug contacts 6 through contact pins 25 (FIG. 5). A cam 26 is provided at the outer periphery of the disk-like carrier portion 23, said cam having two surfaces at its free end, including an angle of approximately 120° with one another.

A second rotating joint member 27 basically consists of the almost closed ring, which evolved from the coating of the connecting conduits 10, formed as a quarter of a ring (compare FIGS. 2 and 3) and of the web 17, connected thereto, which comprises a number of recesses.

If the device according to the invention is installed, the carrier portion 23 of the first rotating joint member 22 engages the annular second rotating joint member 17. The cam 26 formed at the carrier portion 23 engages into the recesses 18, formed at the inner wall of the second rotating joint member. If the plug 5 is rotated with the first rotating joint member attached thereto with respect to the housing, the cam 26 latchingly slides over the recesses 18 of the second rotating joint member. The rotation of the plug 5 with respect to the housing is limited by means of a limiting means, which is not shown in detail, to approximately 90°.

I claim:

1. An electric device for the vaporization of an additive substance comprising:
    a housing having a heating device disposed therein, said heating device comprising a heating element and a heat exchanger, the heat generated by said heating element being conveyed to said heat exchanger, and then conveyed to the substance to be vaporized, wherein said heating element comprises a PTC element clamped between two electrodes, and wherein at least one of said two electrodes is disposed in proximity to said heat exchanger and is integrally formed therewith.

2. A device according to claim 1, further comprising a container connectable to a housing for the substance to be vaporized, and a wick held within said container, and wherein said heat exchanger comprises a passage channel, which surrounds said wick.

3. A device according to claim 2, wherein said heat exchanger is formed annularly having a molded section extending coaxially to said wick.

4. A device according to claim 1, wherein said heat exchanger includes a planar heating surface which serves as a support surface for a container for the substance to be vaporized.

5. A device according to claim 1, wherein said electrodes or the heat exchanger are provided with connecting conduits formed integrally therewith to establish an electrical connection between said heating device and a plug.

6. A device according to claim 5, wherein a region having a reduced wire cross section is provided between said connecting conduits and said electrodes or said heat exchanger.

7. A device according to claim 1, wherein a resilient element is disposed between a said electrode and said PTC element, and a clamping element surrounds the electrode from the outside and keeps the PTC element in close contact to the electrodes.

8. An electric device for the vaporization of an additive substance, comprising:
    a housing having a heating device disposed therein, said heating device comprising a heating element and a heat exchanger, the heat generated by said heating element being conveyed to said heat exchanger, and then conveyed to the substance to be vaporized, wherein said heating element comprises a PTC element clamped between two electrodes and wherein at least one of said two electrodes is disposed in proximity to said heat exchanger and is integrally formed therewith;
    wherein said electrodes or the heat exchanger are provided with connecting conduits formed integrally therewith to establish an electrical connection between said heating device and a plug;
    wherein said connecting conduits, said heat exchanger and said electrodes are integrally formed on a sheet member, which is bent and which is coated by a plastic material at defined points to provide increased stability or heat insulation.

9. A device according to claim 8 wherein said electrodes are surrounded by plastic material on sides opposing one another, and comprise a web at the sides facing said PTC element, formed at the outer edge of said electrode and said PTC element is held in form-fit fashion between said webs.

* * * * *